United States Patent
Palza Cordero et al.

(10) Patent No.: US 11,071,697 B2
(45) Date of Patent: Jul. 27, 2021

(54) METAL-CARBON STRUCTURE HYBRID FORMULATION FOR DENTAL USE IN THE TREATMENT OF DENTAL HYPERSENSITIVITY, DEMINERALIZATION AND CAVITIES

(71) Applicant: UNIVERSIDAD DE CHILE, Santiago (CL)

(72) Inventors: Humberto Cristian Palza Cordero, Santiago (CL); Mario Rodrigo Diaz Dosque, Santiago (CL); Rodrigo Antonio Cabello Ibacache, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 16/461,876

(22) PCT Filed: Nov. 15, 2017

(86) PCT No.: PCT/CL2017/050067
§ 371 (c)(1),
(2) Date: May 17, 2019

(87) PCT Pub. No.: WO2018/090156
PCT Pub. Date: May 24, 2018

(65) Prior Publication Data
US 2019/0365614 A1    Dec. 5, 2019

(30) Foreign Application Priority Data
Nov. 18, 2016   (CL) .................................. 2960-2016

(51) Int. Cl.
*A61K 8/21* (2006.01)
*A61K 8/19* (2006.01)
*A61Q 11/00* (2006.01)

(52) U.S. Cl.
CPC .................. *A61K 8/21* (2013.01); *A61K 8/19* (2013.01); *A61Q 11/00* (2013.01)

(58) Field of Classification Search
CPC ... A61K 8/21; A61K 8/19; A61K 6/20; A61K 45/06; A61K 8/27; A61K 33/02; A61K 33/16; A61K 33/24; A61K 33/30; A61K 33/34; A61K 33/44; A61Q 11/00; C01B 32/23; C01B 32/198; A61P 31/00
See application file for complete search history.

(56) References Cited

U.S. PATENT DOCUMENTS

| | | | |
|---|---|---|---|
| 4,177,258 A * | 12/1979 | Gaffar | A61K 8/21 424/49 |
| 2010/0119461 A1* | 5/2010 | Bicard-Benhamou | A61P 17/08 424/49 |
| 2015/0164085 A1* | 6/2015 | Hall | A61K 8/042 424/638 |

OTHER PUBLICATIONS

Haiwei, J. et al. (Antibacterial applications of graphene-based nanomaterials: Recent achievements and challenges, Apr. 27, 2016) (Year: 2016).*
WO-2018093943-A1 abstract only (Year: 2018).*
CN 106746652 (Year: 2017).*
Batra et al., "Nanoparticles and their Applications in Orthodontics", Adv. Dent. & Oral Health 2(2), 2016; pp. 41-50.
Cheng et al., "Nanotechnology strategies for antibacterial and remineralizing composites and adhesives to tackle dental caries", Nanomedicine (Lond.), 2015, 10(4); pp. 627-641.
Garcia-Contreras et al., "Perspectives for the use of silver nanoparticles in dental practice", International Dental Journal, 2011, 61; pp. 297-301.
Melo et al., "Nanotechnology-based restorative materials for dental caries management", Trends Biotechnol. Aug. 2013, 31(8); pp. 1-18.

* cited by examiner

*Primary Examiner* — Snigdha Maewall
(74) *Attorney, Agent, or Firm* — J.A. Lindeman & Co. PLLC (57) ABSTRACT

The present invention relates to an antibacterial composition which, when applied to the surface of a tooth, allows remineralisation of the enamel to occur, said composition having very low toxicity for human use. When applied, the composition leaves no stains and does not alter the visible colour characteristics of the teeth to which it has been applied.

6 Claims, 6 Drawing Sheets

METAL-CARBON STRUCTURE HYBRID FORMULATION FOR DENTAL USE IN THE TREATMENT OF DENTAL HYPERSENSITIVITY, DEMINERALIZATION AND CAVITIES

TECHNICAL FIELD

The present invention is related to the technical field of compositions or antimicrobial agents which are useful in the dental remineralization.

BACKGROUND AND PRIOR ART

According to data provided by the World Health Organization, between a 60% and 90% of school children have dental caries, and almost 100% of adults have them around the world, wherein the lack of treatment or management can finish in the loss of teeth product of serious diseases associated with their presence. In this situation, between 15 and 20% of adults aged between 35 and 44 years will be ending up losing teeth. At the end of the senior population, close to a 30% of the world population aged between 65 and 74 years does not have natural teeth.

Oral health is essential for good health and a good quality of life.

The dental caries corresponds to a demineralization of the dental tissue, as a result of a unbalance in the environmental conditions of the mouth, mainly the pH or acidity level. This unbalance is caused by the presence of specific microorganisms which generate changes in the acidity due to the presence of sugars or carbohydrates, causing the demineralization process.

The tooth enamel corresponds to a composed bioceramic which provides protection to the tooth. The main component corresponds to a mineral similar to the hydroxyapatite, a calcium orthophosphate of natural occurrence. Specifically, the minerals present in the tooth enamel are composed of calcium, phosphate, and hydroxyl groups, with substituents.

The enamel formation is generated by the action of ameloblasts cells, which are specialized in the formation of the enamel and which allow the formation of the enamel and the transport of the composing minerals. Along with the aforementioned, the ameloblasts allow the orientation during the growth of minerals, which allows generating an organized pattern of growth in the enamel until a mature enamel is obtained.

The mature enamel contains approximately a 95% mineral, a 4% of water, and about 1% of proteins. Precisely this low percentage of proteins provides better properties to the enamel as a high modulus, hardness and low reactivity with the medium.

Particularly, the enamel does not contain cells nor vascularization, therefore, it does not have self-repair or self-remodeling properties. Therefore, the remineralization processes required to obtain a healthy enamel, are governed in a physical chemistry way.

The demineralization of the enamel occurs when local conditions, in particular when the acidity increases, i.e., when the H+ ions increase, which allows that the ions of the minerals which conform the enamel react with the H+ ions releasing themselves toward the solution which surrounds the tooth, i.e., saliva.

One of the main causes of increased acidity in the oral environment, which eventually leads to the demineralization of tooth enamel, corresponds to the presence of bacteria which produce organic acids. Said organic acids affect the pH balance in the oral environment, allowing an acidification, which eventually will produce the demineralization of the enamel.

On the other hand, independent of the cause, when the demineralization process reaches the dentin, it produces another effect associated with dental hypersensitivity. This problem affects up to 50% of the population, although its diagnosis is difficult due to the subjective perception of patients. This phenomenon is associated with a sharp pain that the patient feels by a change in the environmental conditions in the dental environment, mainly by changes in the hydrodynamics, for example, with the temperature. Although there are many causes, all of them seem to be related to an acid erosion. In this way, the remineralization is also a process which helps to the treatment of this demineralization problem.

The remineralization occurs when the concentration of ions in local conditions increases, so that the solution which surrounds the tooth is supersaturated of ions, allowing the deposition of ions on the crystals already formed in the tooth enamel.

The remineralization corresponds to the net gain of calcified material which allows to replace the material that had been previously lost by the demineralization.

The solution to the demineralization of the enamel corresponds to the application of remineralizing agents. A remineralizing agent corresponds to a composition which is capable of promoting remineralization of the dental tissue. Naturally, the saliva results to be a good remineralizing due to phosphate content present in it. In conditions where there is no bacterial plaque responsible for producing organic acids which cause the demineralization of the enamel, the saliva keeps a balance with a biofilm which is formed on the surface of the teeth and the demineralization process. On the contrary, a disruption of said balance, for example, by accumulation of a larger biofilm formed by a greater amount of bacteria, or by an increase in sugars which can be metabolized to organic acids by said bacteria, generates acid conditions sufficient for allowing a demineralization of the enamel.

The injuries produced by the demineralization of the enamel can be classified into non-cavitated dental caries and cavitated dental caries. The first one corresponds to the situation where there is an injury, but due to it is in a sub superficial manner it generates a change in the continuity of the structure and produces a change in reflection index is observed as a white spot. This type of injuries can be treated using chemical means.

On the other hand, the cavitated dental caries correspond to an injury where the surface of the enamel is not macroscopically intact. This latter type of injury requires mechanical treatment using injured-tissue removal turbine and the tooth preparation for the corresponding restorative technique.

The current trend corresponds to apply treatments to avoid reaching cavitated dental caries injuries, so that to avoid the intervention of the piece which implies the loss of that piece in the future which generates a deterioration in the quality of life.

Is in this point where the current treatments appear for allowing the remineralization of the enamel in non-cavitated dental caries cases.

Among the most commonly used remineralizing agents highlights the fluoride, since its function in controlling the development of dental caries injuries, mainly by its topic remineralizing effect has been identified since the 1980s.

There are also another remineralizing agents, such as for example amorphous calcium casein-phosphate phosphopeptides (CPP-ACP, Recaldent®) based on peptides obtained from the casein hydrolysis, wherein said peptides allow the stabilization of amorphous calcium phosphate, facilitating thus, the remineralization of the enamel.

Another remineralizing agent commercially available is bioactive glass (Novamin®) composed of calcium, sodium, phosphorus and silicate. The contact of said material with water allows the release of sodium, calcium and phosphorus ions. The release of calcium generates an increase in the pH and allows the formation of complexes between different ions, helping thus to the remineralization of enamel.

Even though this remineralizing agents are able to improve the mineralization in the tooth, they do not attack the main cause of the dental caries associated with the presence of microorganisms. In this context, the composition of the present invention complies with two requirements: 1) It has the ability of remineralizing the tooth by its ability of forming crystals associated with the composition of the tooth; 2) they have the ability to remove the bacteria responsible of dental caries. Thus, the present invention not only responds to the demineralization consequence, how it achieves remineralize the tooth, but it is capable of facing the cause associated to the presence of bacteria.

Another forms of treatment correspond to cariostatic agents, which stop the progression of dental caries, and which also decrease dental sensitivity, and remineralize the carious dentin. The stannous fluoride and the silver diamino fluoride are examples of these agents. Both agents are toxic, and the former generate blackish-brown pigmentation in teeth treated with them.

On the other hand, the composition of the present invention is a cariostatic and remineralizing agent, but with a much lower toxicity, in addition to not alter the coloration of the tooth.

Therefore, based on the characteristics of the commercial products, there is a need for an agent which can promote the dental remineralization, and which does not present the disadvantages of agents or compounds currently used, more specifically, that this simultaneously be a bacteriostatic agent so that decreasing the bacterial load and which ultimately results in organic acids which damage the teeth enamel. In addition to these properties it is necessary that this agent has low toxicity; and finally, colorless in relation to its application.

In addition, the remineralization not only helps to attack the consequences of dental caries, but it can also help to treat dental hypersensitivity.

The present invention then, corresponds to an agent for treating two dental problems of great impact: 1) dental caries and their consequences associated to the demineralization; and 2) hypersensitivity. Since our invention develops a formulation which have bacteriostatic properties, remineralization effect, low toxicity and coloring effects which are not perceptible after application to the surface of teeth.

In addition, given its characteristics mentioned above, the composition of the present invention may inhibit the demineralization process.

There are some publications of patent applications in the prior art which refer to compositions with some of the features of the present invention, however, none of them meets each and every one of the features of the present invention in terms of its effect. In addition, none of them has the formulation of the present invention.

Some of the documents found are described below:

WO2008089822A2 describes an antibacterial composition, wherein on of its uses dental or oral hygiene is mentioned (prevention of bacterial plaque). The described compositions comprise, among others, metal oxides, wherein the copper is mentioned as one of the options, in addition to metal fluorides (for example magnesium fluoride), graphite is also mentioned as a component of said compositions, wherein the graphite appears as a structural component.

WO2004091567A2 describes compositions with antibacterial properties of topical use. Its use is mentioned for controlling acne or dandruff. Among the components, it is mentioned metal fluorides or mixtures, or metals or oxides thereof and it also mentions graphite as component which provides pigmentation to the formulation, although its use for oral or dental hygiene is not described or suggested.

WO2004092283A2 describes pigments with antimicrobial capabilities. Among the different uses described for said pigments, cosmetic uses are mentioned, within which dental hygiene is included. Products as toothpaste or mouthwash are mentioned, which can contain the mentioned pigments. Among the described components different components with antimicrobial activity are highlighted, metals and oxides thereof are mentioned, wherein copper is specifically mentioned. It is also mentioned that it can contain fluorine in the form of magnesium fluoride (among others).

SUMMARY OF THE INVENTION

The present invention corresponds to a composition with antibacterial activity, and which applied to a dental surface allows the remineralization of the enamel, wherein the composition has a low toxicity for human use, and wherein its application does not leave stains nor change the visible color features in dental pieces wherein the composition has been applied.

DETAILED DESCRIPTION OF THE INVENTION

In a first aspect, the invention corresponds to a composition or antimicrobial agent which also promotes the remineralization of the surface of tooth and dentin enamel.

In a particular embodiment, the composition comprises at least 3 components selected among:
  i. An inorganic antimicrobial agent;
  ii. An agent which promotes the remineralization of a surface of tooth and dentin enamel;
  iii. An agent which inhibits the demineralization of tooth and dentin enamel; and
  iv. A stabilizing agent which may also have antimicrobial properties and can help to the remineralization.

In a more specific embodiment, the inorganic antimicrobial agent is selected from metals and their salts, oxides and/or complexes, including copper, zinc, tin, and molybdenum derivatives, such as ammonia complexes of these metals, in a high concentration controlled by the addition of a solubilizing agent selected from different ammonia solutions. The ammonia solution is presented in a range of concentration in water between 1 and 50% v/v.

In another specific embodiment, the promoter of remineralization is selected among halogens, in particular, fluorides compounds, to which it can also add another particulate mineralizing agents, such as ceramics. These same promoters can also inhibit the demineralization of the tooth.

In another specific embodiment, the stabilizing agent is selected from different carbon structures, specifically, those derived from the graphene and/or graphite, more specifically from graphite oxides and graphene oxides, and when the stabilizing agent is selected from graphite oxides and graphene oxides, said stabilizing agent also presents antimicrobial properties and helps the remineralization.

In particular, without the intention of limiting the scope of the invention, the more preferred components correspond to copper complexes with fluorine. More specifically, the copper is composed by a copper ammonia complex whose counterion is $(Cu(NH_3)_6)F_2$ fluoride to a high pH, typically between 8-12; the more preferred remineralization promoter agent and the demineralization inhibitor is fluorine; and the more preferred stabilizing agent is a derivate from graphite, more specifically a graphite oxide or graphene oxide.

In a more specific embodiment, the composition of the present invention also comprises another stabilizing agents derived from carbon, such as graphene, and its oxides. In yet another more specific embodiment the antimicrobial and remineralizing agent, in particular $(Cu(NH_3)_6)F_2$, is present at a concentration of between 100 and 40,000 ppm, and the stabilizing agent, in particular a derivate from graphene oxide type graphite, is in a concentration of between 0.0001 and 0.02 g/ml.

EXAMPLES OF APPLICATION

Example 1: In Vitro Evaluation of the Antibacterial Capacity

Figure 1:
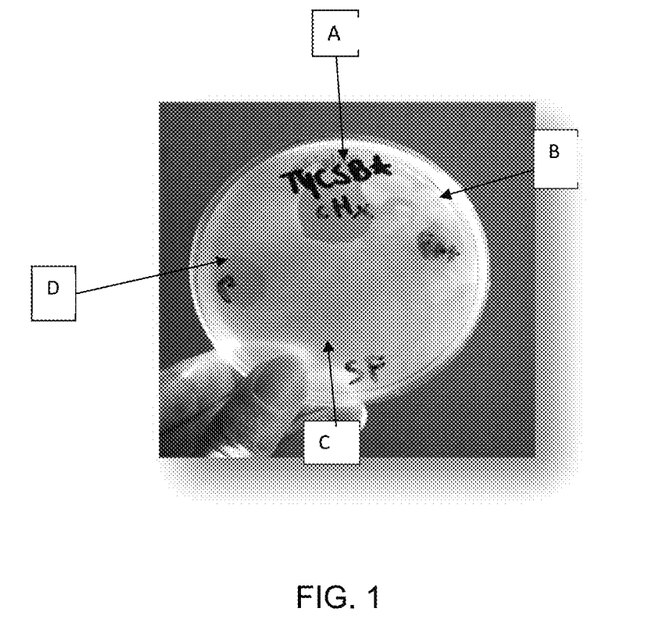
FIG. 1. Photograph comparing the antimicrobial effect against microorganisms of the dental caries, from different commercial products and the composition of the present invention. The dark zone corresponds to the area where there is no bacterial growth. Composition of the present invention which possess a similar ability to Silver Diamine Fluorine. A) Chlorhexidine, B) Silver Diamine Fluorine, C) Silane Fluorine, D) Composition of the Invention.

Tests to demonstrate the antibacterial effect of the composition of the present invention were performed, in particular using 25,000 ppm of an aqueous solution of $(Cu(NH_3)_6)F_2$ ammonia in presence of 0.002 g/ml of graphite oxide, comparing it with products which are currently available in the market and which is considered the standard in the field. These tests have been performed on the main bacterial species associated with dental caries. It is concluded that the composition of the present invention has the ability to remove the bacteria related with the dental caries to a similar level than other commercial products. It is only exceeded by chlorhexidine, which is a very active compound, but it does not have the other functionalities presented by the composition of the present invention, which is observed in FIG. 1, where the areas of inhibition halos for chlorhexidine is 659 $mm^2$; Product on the market 200 $mm^2$; composition of the present invention 278 $mm^2$.

Example 2: In Vitro Evaluation of Cytotoxicity

Figure 2:
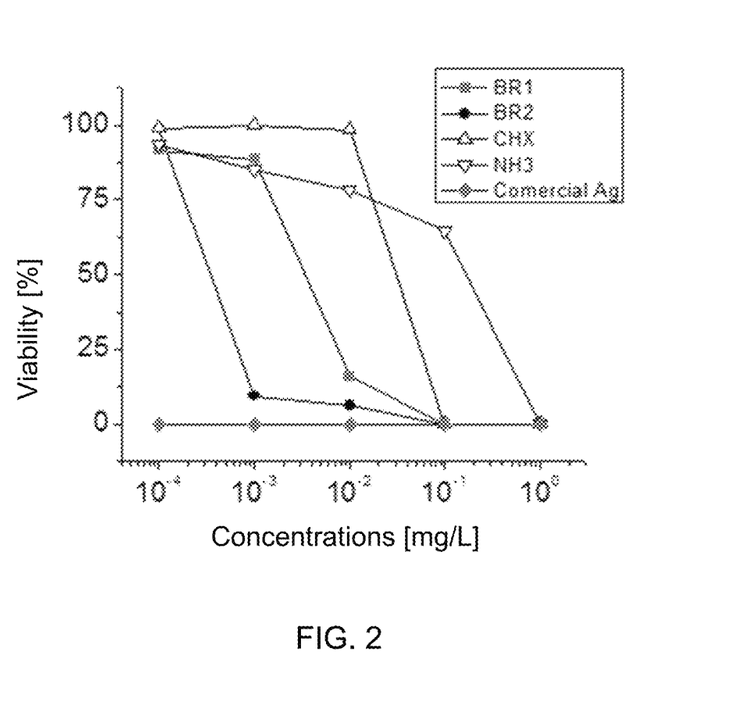
FIG. 2. Cell viability assay using mitochondrial activity technique (MTT). THP1 cell type. Commercial=(Silver Amino Fluorine Commercial Product), White, CHX=Chlorhexidine, BR1 and BR2=example of compositions of the present invention.

To evaluate the cytotoxicity of the composition of the present invention, viability experiments were performed of a cell culture exposed to the composition of the present invention. In particular, the viability of (TPH1) human cells was quantified by a mitochondrial activity assay (MTT) in contact with different concentrations of the composition of the present invention. In addition, this result was compared to other commercial products currently used in clinical practice routine. It is observed that the commercial product is extremely toxic (0% viability) independent of the used dilution. On the other hand, the composition of the present invention, in its formulation with and without the stabilizing, presents high viability to dilutions of the order of $10^3$ o $10^4$. It is also observed that any product, including the chlorhexidine, present a degree of toxicity, therefore, what is the most important is that the composition of the present invention is much less toxic than the commercially available alternatives (FIG. 2).

Example 3: Ability of Remineralization Using an In Vitro Model of Dental Caries At this stage it is aimed to evaluate in an in vitro model the remineralizing ability of the composition of the present invention. It has been mounted an in vitro model of dental caries lesions development by the metabolic activity of microbial species on human teeth by a monospecie biofilm. This allows you to produce lesions similar to those that occur in a real-world scenario.

Figure 3:
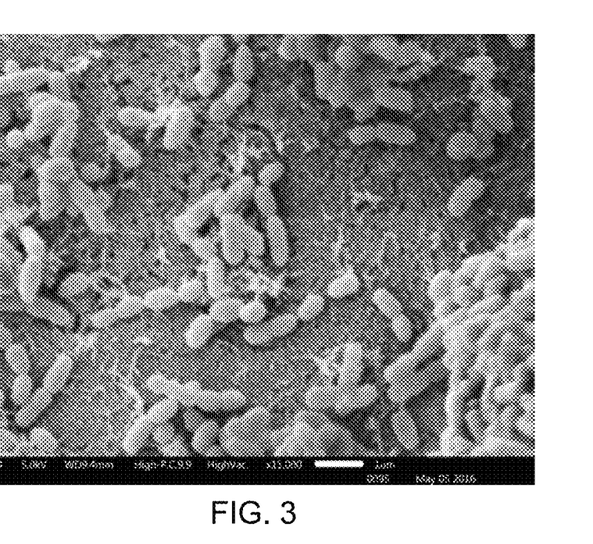
FIG. 3. Scanning electron micrograph (SEM) of a biofilm formed by *Streptococcus* mutants on synthetic hydroxyapatite surface.
Figure 4:
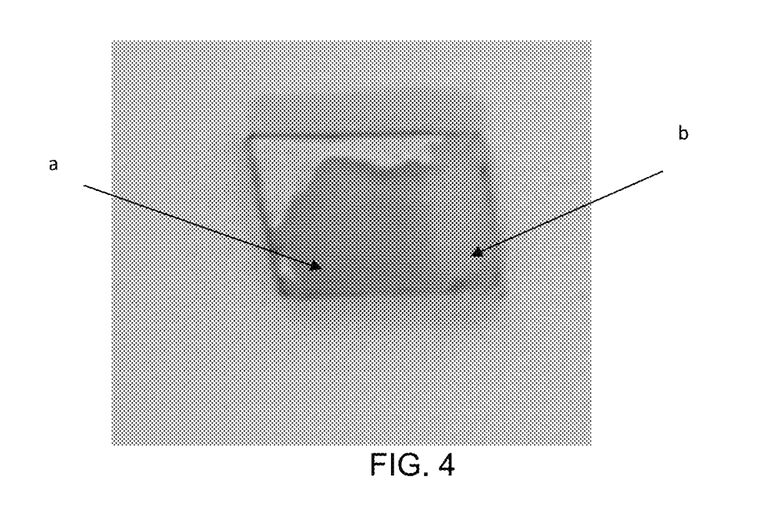
FIG. 4. Photograph which shows a section of a) demineralized dentin by the biofilm effect and b) Non-demineralized dentin. White area is tooth enamel demineralized waste.

Our first result is related to validate the microbiological model of in vitro dental caries. The dental caries model described by Ccahuana-Vásquez y Cury (2010 April-June; 24(2):135-41) was used, in which the simulation of a cariogenic environment is carried out by the exposure of enamel blocks, dentin or calcium hydroxyapatite to sucrose, previous formation of a monospecie biofilm of *Streptococcus mutans*. (FIG. 3) Thus, it is allowed to obtain a demineralization zone, which can then be remineralized with an experimental remineralizing agent.

The lesions of non-cavitated artificial dental caries generated according the previous protocol, are subjected to different protocols of remineralization using different concentrations and exposure times to a composition according to the described in the present invention. In addition, differences in the remineralization between this product with those currently used for this purpose will be determined.

Figure 5:
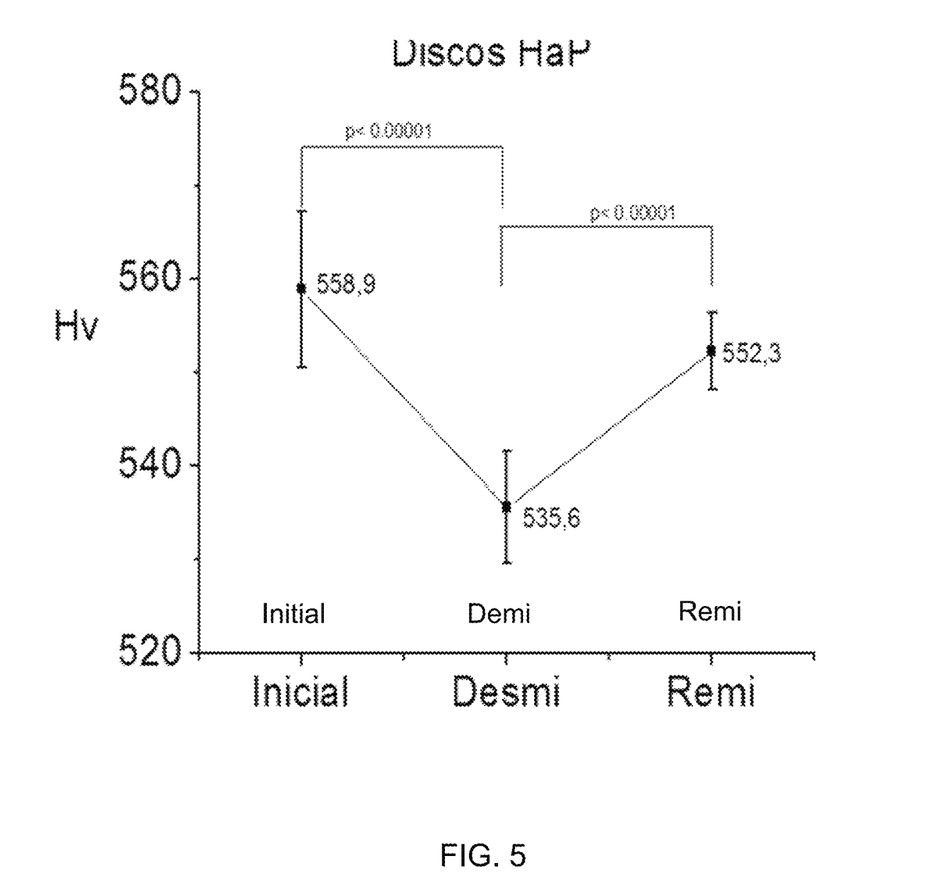
FIG. 5. Vickers microhardness of hydroxyapatite disks (HaP). The values of not microbiologically treated dentin (initial), demineralized by the developed microbiological in-vitro model (Desmi) and after applying a composition of the present invention (Remi), are shown. The bar indicates its maximum and minimum value. Statistically significant difference is indicated with a $p<0.00001$ ($n=90$), and in a confidence interval of 95%.

For the evaluation of the remineralizing effects, indicators of tissue superficial hardness change (Vickers microhardness) will be used, the obtained results obtained are given account below:

Hydroxyapatite Disks:

According to the obtained data (n=90) the initial hardness of the Hydroxyapatite disks (HAP) is of 5,480.9 MPa with a confidence interval of 95% between 5,398.6 MPa and 5,562.3 MPa. After the specimens were subjected to the in vitro model of dental caries lesions development simulating the conditions of the mouth the hardness is 5,262.2 MPa with a confidence interval between 5,192.6 y 5,311.3. This difference between the initial disk and the treated one in the dental caries model, are statistically significant with $p<0.0001$. After the specimens were subjected to the remineralization protocol with the composition of the present invention, the hardness values are 5,416.2 MPa with an interval of 95% confidence between 5,375 and 5,456.4. The average difference observed is of 228.5 MPa with a confidence interval of 95% between 130.4 and 326. (FIG. 5). This difference is statistically significant when is compared with the controls with a value $p<0.00001$. Therefore, it is demonstrated that the presence of the composition of the present invention increases the hardness of the injured material to values close to which the system had before the injury. This is an indicator that the composition product of the present invention is able to remineralize.

Figure 6:
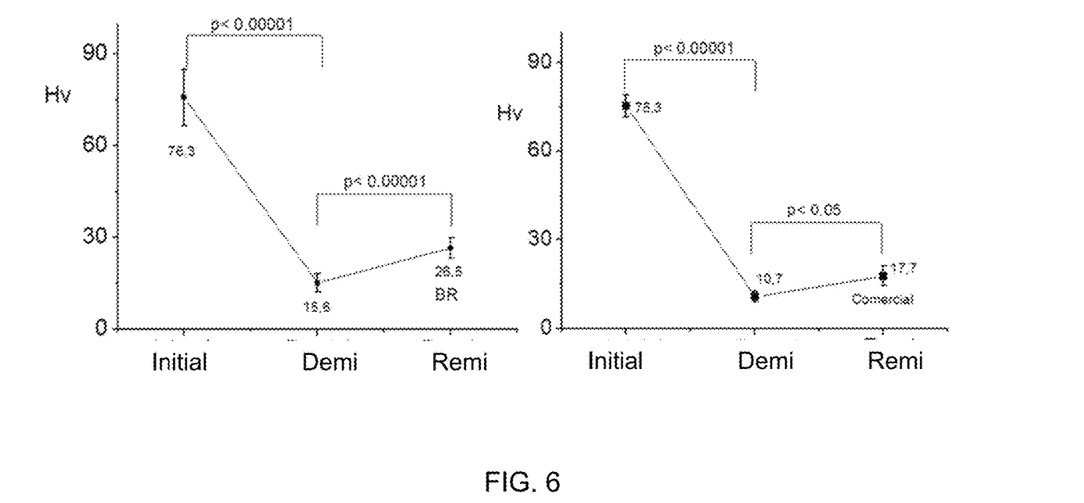
FIG. 6. Dentin Vickers microhardness. The values of not microbiologically treated dentin (initial), demineralized by the developed microbiological in-vitro model (Desmi) and after applying a composition of the present invention (Remi) are shown. Left chart composition effect of the present invention and right chart commercial agent effect. The bar indicates its maximum and minimum value. Statistically significant difference is indicated with a $p<0.00001$ o $p<0.05$, as appropriate ($n=90$), for a confidence interval of 95%. There is no significant statistical difference between the increase with respect to the sample remineralized with composition of the present invention and with the commercial product.
Figure 7:
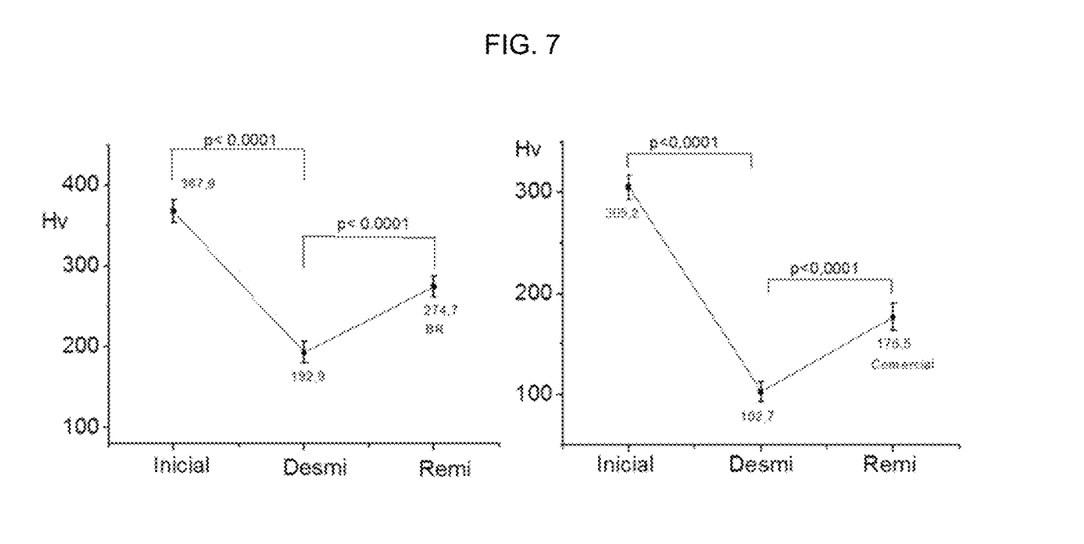
FIG. 7. Vickers microhardness of enamel. The bar indicates its maximum and minimum value. The values of not microbiologically treated enamel (initial), demineralized by the developed microbiological in-vitro model (Desmi) and after applying a composition of the present invention (Remi) are shown. Left chart composition effect of the present invention and right chart commercial agent effect. Statistically significant difference is indicated with a $p<0.00001$ (n=90), for a confidence interval of 95%. There is no significant statistical difference between the increase with respect to the sample remineralized with composition of the present invention and with the commercial product.

Dentin and Enamel:

Real teeth were also evaluated (FIGS. 6 and 7). Dentin has an initial value of 748.2 MPa, which after being subjected to the in vitro demineralization decreases to 152.9 MPa. Using our formulation of the present invention, this value increases to 259.9 MPa, with a statistical significance ($p<0.00001$) In the enamel the trend is the same. In both cases, the commercial product presents the same increases in hardness in our materials.

Figure 8:
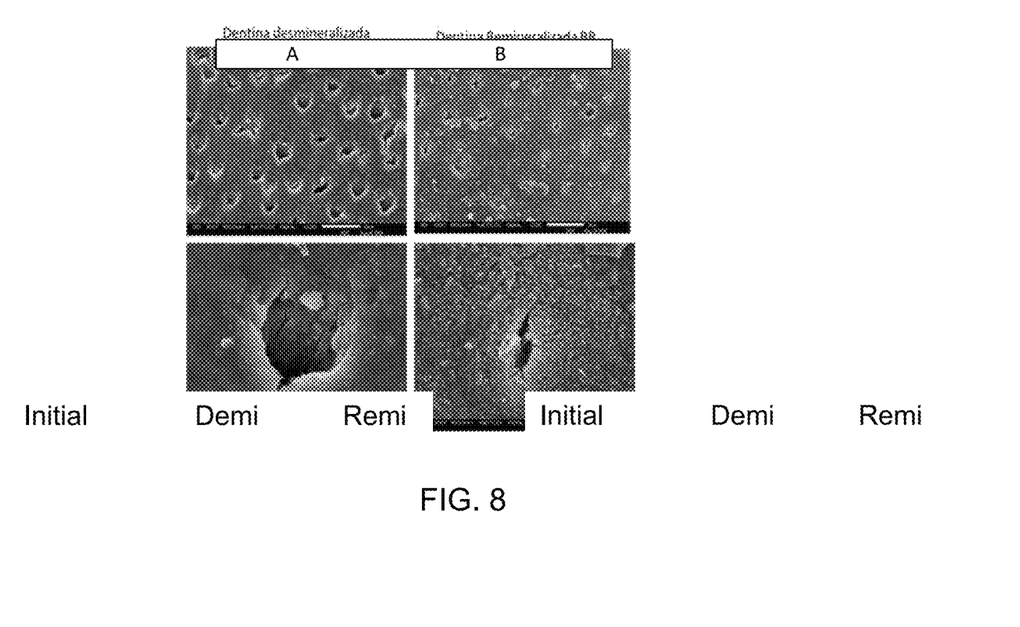
FIG. 8. Micrographs by scanning electron microscopy (SEM) of demineralized dentin before (A) and after (B) of applying a composition of the present invention.
Figure 9:
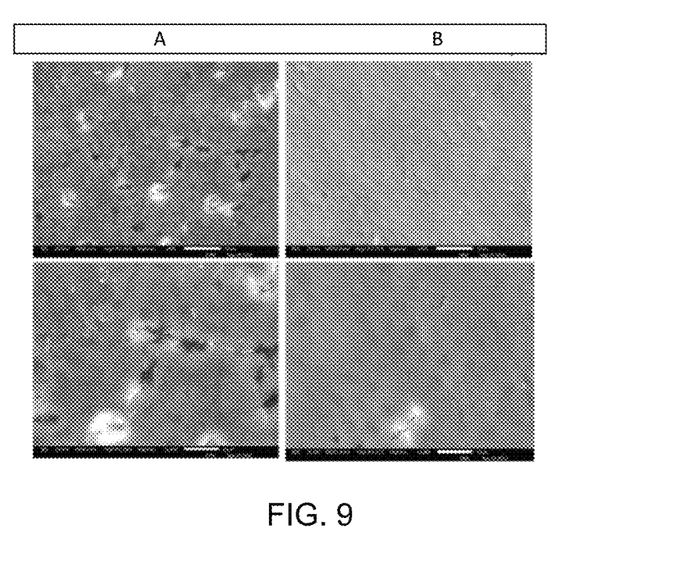
FIG. 9. Micrographs by scanning electron microscopy (SEM) of demineralized enamel before (A) and after (B) of applying a composition of the present invention.
Figure 10:
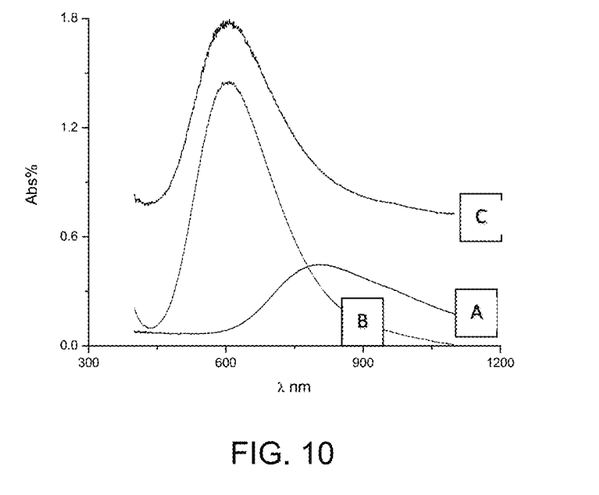
FIG. 10. UV-Vis spectrum of components of the composition of the present invention and their interactions: A: $Cu(H_2O)_6F_2$; B: $Cu(NH_3)_6F_2$; C: $Cu(NH_3)_6F_2+GO$.

The remineralizing ability of our formulation is confirmed by micrographs by scanning electron microscopy (SEM) of dentin and enamel, demineralized and after applying composition of the present invention. It is clearly observed that the samples after being subjected to composition of the present invention present an associated closure to the remineralization.

Example 4: Evaluation of the Molecular Interaction of Components of the Composition of the Present Invention The composition of the present invention has been characterized as a metal in solution, but as ammonia complex of theoretical formula of $Cu(NH_3)_6F_2$. In FIG. 6 it is observed the absorption spectrum UV/Visible which confirms this structure.

The shift toward smaller wavelengths gives an account of the formation of ammonia metal complex which is observed in an increase of the solubility of the salt in this solution which allows to reach fluoride concentrations close to 30,000 ppm, which is impossible in aqueous solution.

INDUSTRIAL APPLICATION

The present invention finds application in the pharmaceutical or cosmetics industry, more specifically in the production of compositions for the care of oral health.

The invention claimed is:

1. A composition having antimicrobial activity and which also promotes the remineralization of the surface of tooth enamel and dentin, comprising: a) an inorganic antimicrobial agent selected from the group consisting of copper, zinc, tin, and molybdenum, salts, oxides, and complexes thereof, wherein the inorganic antimicrobial agent is present in a concentration controlled by the addition of a solubilizing agent selected from solutions of ammonia;
   b) a promoter agent of remineralization of a surface of tooth enamel and dentin wherein the promoter agent comprises an ammonia complex of copper whose counter ion is fluoride ($Cu(NH_3)_6)F_2$ at a pH between 8 and 12;
   c) an inhibitor agent of the demineralization of tooth enamel and dentin; and
   d) a stabilizing agent having antimicrobial properties and which also helps the remineralization selected from the group consisting of derivatives of graphite oxides, graphene oxides, and mixtures thereof,
   wherein the promoter agent of remineralization, ($Cu(NH_3)_5)F_2$, is present in a concentration of between 100 and 40,000 ppm, and it also has an antimicrobial activity.

2. The composition according to claim 1, wherein the ammonia solution is present in a range of concentration in water between 1 and 50% v/v.

3. The composition according to claim 1, wherein the inhibitor agent of the demineralization is selected from halogen compounds.

4. The composition according to claim 1, wherein the stabilizing agent is present in a concentration of between 0.0001 and 0.02 g/ml.

5. The composition according to claim 3, wherein the inhibitor agent of the demineralization is selected from fluoride compounds.

6. The composition according to claim 1, wherein the inorganic antimicrobial agent is an ammonia complex of copper, zinc, tin, or molybdenum.

* * * * *